United States Patent
Cheng et al.

(10) Patent No.: US 12,382,135 B2
(45) Date of Patent: Aug. 5, 2025

(54) TELEVISION USE ASSESSMENT SYSTEM

(71) Applicant: Logistics and Supply Chain MultiTech R&D Centre Limited, Pok Fu Lam (HK)

(72) Inventors: Chun Hung Cheng, Pok Fu Lam (HK); Ka Man Ng, Pok Fu Lam (HK); Tsz Kin Chan, Pok Fu Lam (HK); Chi Fung Chan, Pok Fu Lam (HK); Woon Kwai Ngai, Pok Fu Lam (HK)

(73) Assignee: Logistics and Supply Chain MultiTech R&D Centre Limited, Pok Fu Lam (HK)

( * ) Notice: Subject to any disclaimer, the term of this patent is extended or adjusted under 35 U.S.C. 154(b) by 25 days.

(21) Appl. No.: 18/406,684

(22) Filed: Jan. 8, 2024

(65) Prior Publication Data
US 2025/0227328 A1 Jul. 10, 2025

(51) Int. Cl.
*H04N 21/442* (2011.01)
*G16H 20/30* (2018.01)
*G16H 50/30* (2018.01)
*H04N 21/422* (2011.01)

(52) U.S. Cl.
CPC ....... *H04N 21/44218* (2013.01); *G16H 20/30* (2018.01); *G16H 50/30* (2018.01); *H04N 21/42204* (2013.01)

(58) Field of Classification Search
CPC ....... H04N 21/44218; H04N 21/42204; G16H 20/30; G16H 50/30
See application file for complete search history.

(56) References Cited

U.S. PATENT DOCUMENTS

| | | | |
|---|---|---|---|
| 2017/0251972 A1* | 9/2017 | Jayaraman | A61B 5/1118 |
| 2021/0322856 A1* | 10/2021 | Virkar | H04N 7/147 |
| 2021/0342952 A1* | 11/2021 | Putnam | H04N 21/47202 |
| 2022/0054892 A1* | 2/2022 | North | A61B 5/744 |
| 2022/0110548 A1* | 4/2022 | Radwin | A61B 5/0022 |
| 2022/0296966 A1* | 9/2022 | Asikainen | G16H 20/30 |
| 2022/0313118 A1* | 10/2022 | Elhawary | G06F 18/00 |
| 2022/0366811 A1* | 11/2022 | Donnelly | G06T 7/20 |

FOREIGN PATENT DOCUMENTS

CN 112272324 3/2023

* cited by examiner

*Primary Examiner* — Oschta I Montoya
(74) *Attorney, Agent, or Firm* — Renner, Kenner, Greive, Bobak, Taylor & Weber (57) ABSTRACT

A television (TV) use assessment system includes a TV decoder device operatively coupled to a television (TV) and configured to receive signals, decode the received signals and provide an output to be presented on a TV; a remote control device configured to receive inputs from a user and transmit input signals to the TV decoder device, wherein the TV decoder device is configured to receive the input signals from the remote control device and perform one or more functions encoded within the input signals; a camera configured to record user interactions with the system; and a performance evaluation apparatus configured to: receive the recording of the user interacting with the system and analyse the recording to generate an evaluation of the user interactions.

12 Claims, 7 Drawing Sheets

TELEVISION USE ASSESSMENT SYSTEM

TECHNICAL FIELD

The present invention relates to a television (TV) use assessment system, in particular a TV training and use assessment system.

BACKGROUND

Televisions (TVs) are ubiquitous in many homes. Many users still use a TV decoder device on their TV to receive signals and decode the received signals. TV set top boxes (or cable box) are an example of TV decoder devices that are still commonly used. A TV set top box connects to the TV, and in use is configured to receive and convert satellite or digital signals or internet data to TV signals so video content can be presented on the TV.

A remote control device is generally used to provide input signals to interact with the TV set top box and control the operations of the TV set top box. Many impaired users especially elderly uses cannot use touch screens or cursor-based application (app) in a smart device (e.g., a mobile phone or tablet) very well. Most TV set top box user interfaces are navigated using an app on a smart device or by using the cursor buttons on a remote control device (e.g., a standard TV remote control device). The various functions and options of the TV set top box are navigated and selected by a cursor functionality from a remote control device or an app on a smart device. Elderly users often lack the dexterity and the vision and find it very difficult to control a cursor via an app or a remote control device. This makes usability of a TV set top box very difficult or not possible in some instances. This can lead to frustration and at times boredom for elderly users. Similar frustrations can occur for other impaired users e.g., physically impaired users that lack the finger and/or hand dexterity to control a cursor on a remote control device or a cursor provided via an app on a smart device.

Additionally, there is currently no commonly used method to objectively assess the use of a TV set top box by an impaired user e.g., an elderly user. Currently there no common approaches to objectively assess the performance of how well a user interacts with a TV set top box using a remote control device or an app. Current TV set top box assessment systems use a camera to capture a video of a user using the set top box. The captured video is uploaded to a backend system for a therapist (e.g., a physical therapist or occupational therapist or physiotherapist) to view. The user performance is subjectively assessed by the therapist, and there isn't objective assessment or objective comparison between users.

SUMMARY OF THE INVENTION

According to a first aspect, there is provided a television (TV) use assessment system comprising:
a TV decoder device operatively coupled to a television (TV) and configured to receive signals, decode the received signals and provide an output to be presented on a TV,
a remote control device configured to receive inputs from a user and transmit input signals to the TV decoder device,
wherein the TV decoder device is configured to receive the input signals from the remote control device and perform one or more functions encoded within the input signals, a camera configured to record user interactions with the system,
a performance evaluation apparatus configured to: receive the recording of the user interacting with the system and analyse the recording to generate an evaluation of the user interactions.

In one example the performance evaluation is a performance score that is indicative of how well a user is interacting with the system, and the performance score being generated by the performance evaluation apparatus.

In one example:
the TV decoder device is configured to output a training video that is presented on the TV,
the camera is configured to record the interactions with the system,
the performance evaluation apparatus configured to:
receive the recorded interactions,
compare the recorded interactions with the training video,
generate the performance score based on the comparison of the recorded interactions and the training video,
present the performance score on a display or transmitting the performance score to a therapist device.

In one example the TV decoder may be configured to wirelessly communicate with the performance evaluation apparatus and the TV decoder device is configured to receive the training video from the performance evaluation apparatus.

In one example the performance evaluation apparatus is further configured to:
compare the performance score with a performance threshold,
generate an alert if the performance score is less than the performance threshold,
transmit the alert and performance score to a therapist device and/or present the alert and performance score on the TV or on a display of the performance evaluation apparatus.

In one example a performance score less than a performance threshold is indicative of a user at risk of injury.

In one example the performance evaluation apparatus comprises:
a scoring module configured to calculate the performance score based on the comparison between the recorded interactions and the training video, and
a risk module configured to calculate a risk profile for a user based on the performance score calculated in the scoring module, the risk profile being indicative of the likelihood of an injury occurring to the user.

In one example the risk module is configured to calculate the risk profile based on the difference between performance score of the user and the performance threshold, wherein the higher the performance score the lower the risk profile.

In one example the camera is configured to detect a video of a user interacting with the remote control device and providing inputs to the TV decoder.

In one example the recorded interactions are a video of the user's interactions with the system, and the performance evaluation apparatus configured to perform an object recognition process on the recorded video and the training video to: identify a user or one or more limbs of the user, identify the movements performed by the user and compare the identified movements with the training video.

In one example, the performance evaluation process may comprise a machine learning model or an AI model that is trained to execute an object detection process on the received recordings i.e., the received video recording and identify the interactions of the user with the remote control device and the TV decoder device.

In one example the performance score is an objective score calculated by the performance evaluation apparatus.

In one example the TV decoder device comprises:
an application interface that, in use, is presented on the TV,
wherein the application interface defines one or more functions of the TV decoder device,
the application interface comprises one or more buttons, wherein each button comprises an alphanumeric character or a symbol,
each button corresponding to a function of the one or more functions, and;
each button being selectable from a user input at the remote control device.

In one example the application interface comprises at least twelve buttons, at least two buttons comprising a symbol and at least ten buttons comprising numerals.

In one example the remote control device comprises a plurality of physical buttons,
the application interface buttons are activatable virtual buttons, wherein each virtual button is associated with a specific function of the TV decoder device,
wherein the application interface buttons are virtual buttons that correspond to the arrangement of the remote control device physical buttons, such that a physical button pushed on the remote control device is configured to cause the corresponding application interface button to be activated, and;
the TV decoder device is configured to execute a function associated with the activated application interface button.

In one example the application interface virtual buttons are arranged in a configuration that substantially matches a button configuration of a landline telephone, and the remote control device physical buttons are arranged in configuration that substantially matches the button configuration of a landline telephone, and wherein the virtual buttons and physical buttons are identical in configuration.

In one example the TV decoder is a TV set top box and the camera is integrated into the TV decoder.

In one example the TV use assessment system comprises a speaker, the speaker being operatively coupled to the TV decoder device and controlled to provide voice commands to a user to guide a user to use the TV remote device to control the application interface.

In one example, the speaker may be integrated into the TV decoder device. In another example, the speaker may be a speaker of the TV that is controlled by the TV decoder. In a further example, the TV decoder may be configured to communicate with a user device e.g., a mobile phone or tablet and the speaker may be a user device speaker.

According to a second aspect, there is provided a remote control device for use in a TV use assessment system comprising:
a body,
a transmitter configured to transmit signals to a TV decoder device of the TV use assessment system,
a plurality of physical buttons, wherein at least two of the physical buttons comprise symbols and at least two of the physical buttons comprise alphanumeric characters,
wherein actuating a physical button causes an input signal to be transmitted to the TV decoder device causing the TV decoder device to perform a predefined function associated with the button.

In one example the remote control device may comprise a power source e.g., a battery. The remote control device may optionally include a receiver to receive communications from a user device or the TV decoder device. In one example, the remote control device may be configured to wirelessly communicate with the performance evaluation apparatus.

In one example the physical buttons comprise at least twelve buttons, wherein at least ten buttons that each comprise a numeral, the numerals being 0 to 9, and at least two buttons comprising distinct symbols, wherein one button comprises a * symbol and the other button comprises # symbol.

In one example the physical buttons are arranged in a configuration that matches the configuration of buttons on a landline telephone.

In a third aspect, there is provided a computer implemented method of TV use assessment comprising the steps of:
receiving recorded interactions of a user with a remote control device and a TV decoder device,
comparing the recorded interactions with the training video,
generating the performance score based on the comparison of the recorded interactions and the training video,
presenting the performance score on a display or transmitting the performance score to a therapist device. In one example, the performance score that is indicative of how well a user is interacting with the system, and the performance score is generated by a performance evaluation apparatus.

In one example the method comprises
comparing the performance score with a performance threshold,
generating an alert if the performance score is less than the performance threshold,
transmitting the alert and performance score to a therapist device and/or present the alert and performance score on the TV or on a display of the performance evaluation apparatus. In one example a performance score less than a performance threshold is indicative of a user at risk of injury.

A computer program comprising instructions which, when the program is executed by a computer, cause the computer to carry out the method of TV use assessment described above.

A computer-readable medium comprising instructions which, when executed by a computer, cause the computer to carry out the method of TV use assessment described above.

A data processing apparatus comprising a processing device or processor for carrying out the method of TV use assessment.

The term "comprising" (and its grammatical variations) as used herein are used in the inclusive sense of "having" or "including" and not in the sense of "consisting only of".

It is to be understood that, if any prior art information is referred to herein, such reference does not constitute an admission that the information forms a part of the common general knowledge in the art.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENTS

The present invention relates to a television (TV) use assessment system, in particular a TV training and use assessment system for training an impaired user and assessing the performance of the user. The TV use assessment system is particularly suited for assessing the use of TV set top box by an impaired user. The impaired user may be person that has mental and/or physical impairment e.g., an elderly person or a person with arthritis or another chronic condition. The assessment system is advantageous because it provides objective assessment of how a user has used the TV decoder device. The system further can provide for objective comparison between different users.

The present invention further relates to a remote control device providing a simplified user interface that, in use, is configured to communicate with a TV decoder device. The remote control device with a simplified user interface comprises a plurality of buttons wherein each button corresponds to a specific control function of the TV decoder device. The remote control device is used as part of the TV use assessment system. The remote control device is advantageous because it provides a simpler and more useable interface to allow impaired users (e.g., elderly users) to interact with and operate the TV decoder device (i.e., TV set top box).

Figure 1:
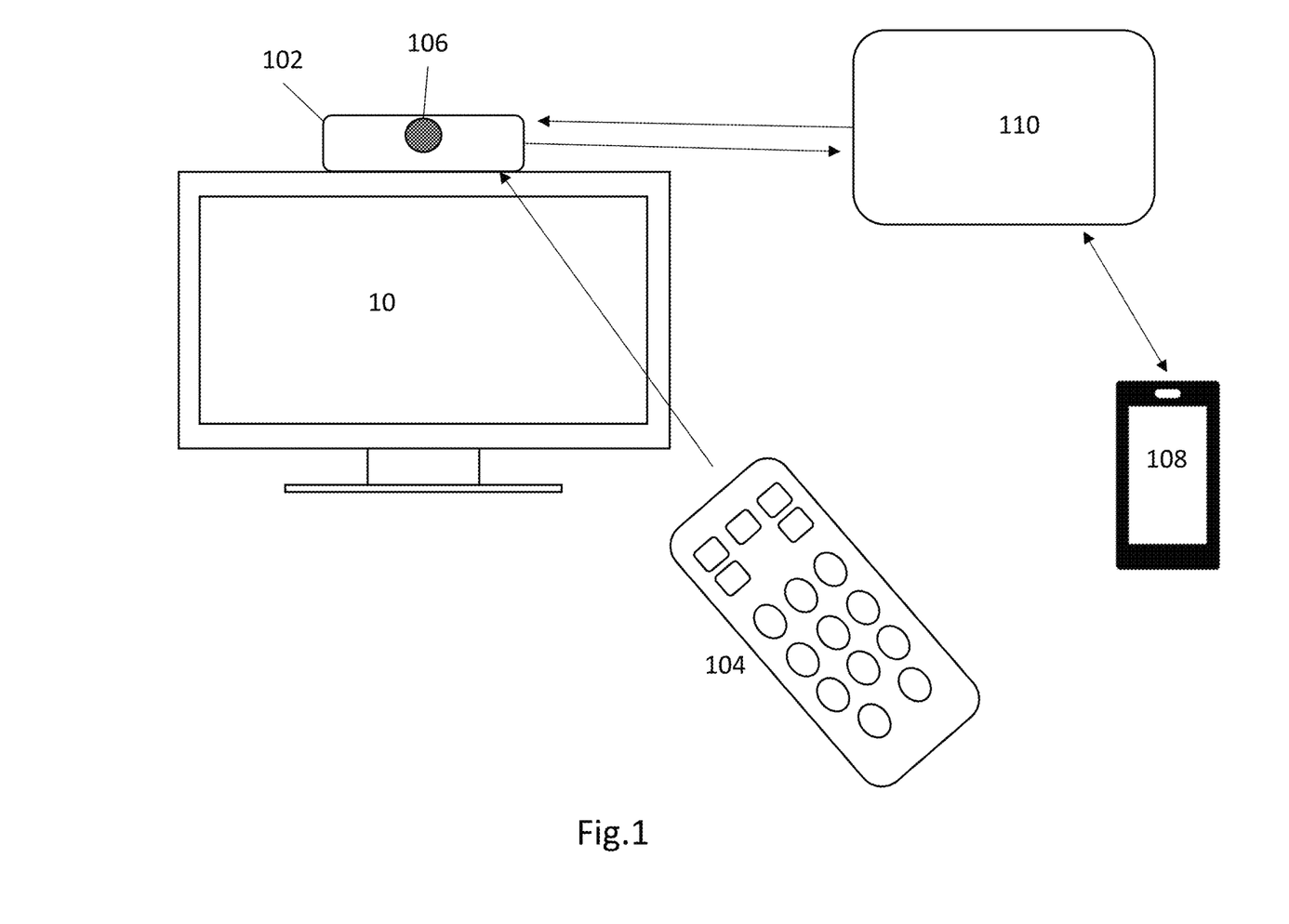
FIG. 1 illustrates an example embodiment of a TV use assessment system.

Referring to FIG. 1, an embodiment of the present invention is illustrated. This embodiment is arranged to provide a TV use assessment system 100 comprising: a TV decoder 102 operatively coupled to a TV 10, a remote control device 104, a camera 106 and a performance evaluation apparatus 110. The TV decoder device 102 operatively coupled to a television (TV) 10 and configured to receive signals, decode the received signals and provide an output to be presented on a TV 10. The remote control device 104 is configured to receive inputs from a user and transmit input signals to the TV decoder device 102. The TV decoder device 102 is configured to receive the input signals from the remote control device 104 and perform one or more functions encoded within the input signals. The camera 106 is configured to record user interactions with the system 100. The performance evaluation apparatus 110 is configured to: receive the recording of the user interacting with the system and analyse the recording to generate an evaluation of the user interactions. The performance evaluation apparatus 110 is configured to communicate with a therapist device 108, preferably, via a portal.

The performance evaluation is a performance score that is indicative of how well a user is interacting with the system, and the performance score being generated by the performance evaluation apparatus. The performance score may be transmitted to the therapist device 108. The performance score may be presented on the TV 10. The TV 10 may be any suitable television e.g., an LCD or LED TV.

The TV decoder device 102 may be a device that operatively connects to the Television (TV) 10, and converts cable, satellite or digital signals or internet data to TV signals so video content can be displayed or presented on the TV 10 for viewing by a user. The TV decoder device 102 may be a separate device to the TV. Alternatively, the TV decoder device 102 may be integrated into the TV 10. The TV decoder device 102 may be a TV set top box. The TV set top box 102 is configured to receive signals from the remote control device 104. The TV set top box 102 is adapted to execute one or more predefined functions that are associated with the buttons of the remote control 104.

The remote control 104 comprises a body and a transmitter that is configured to transmit signals to the TV decoder device 102. The remote control device 104 comprises a plurality of physical buttons. The remote control 104 comprises at least two of the physical buttons comprising symbols and at least two of the physical buttons comprising alphanumeric characters. Actuating a physical buttons causes an input signal to be transmitted to the TV decoder device causing the TV decoder device to perform a pre-defined function associated with the button.

Figure 2:
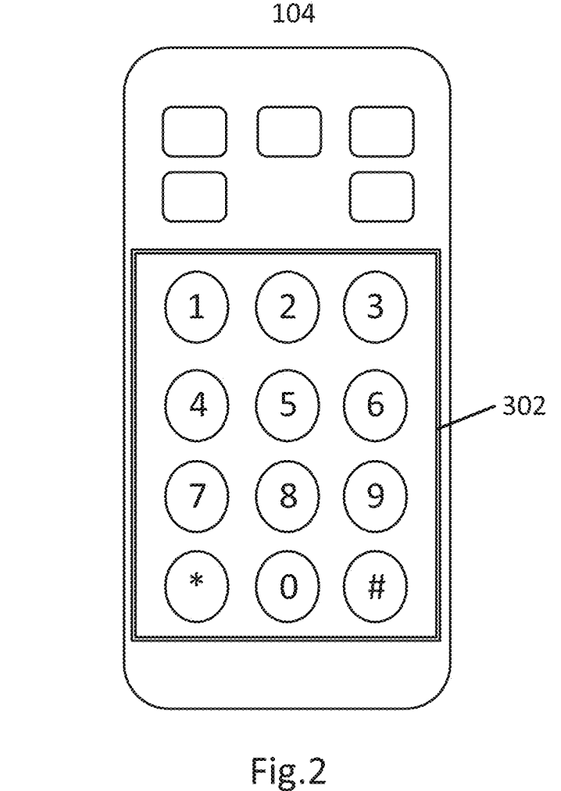
FIG. 2 illustrates an example of a remote control device that forms part of the system of FIG. 1 and an example button configuration of the remote control device.

FIG. 2 illustrates an example of the remote control device 104. The Referring to FIG. 2, the physical buttons comprise at least twelve buttons. The remote control device 104 comprises at least ten buttons that each comprise a numeral wherein the numerals being 0 to 9, and at least two buttons comprising distinct symbols, wherein one button comprises a * symbol and the other button comprises # symbol. One button may comprise a < symbol. In the illustrated example the remote control device 104 comprises ten buttons each having a numeral. The numerals are 0-9. One button comprises the symbol # and the one button comprises * symbol. The remote control 104 may comprise additional buttons.

The remote control device 104 may comprise a power source e.g., a battery. The remote control device may optionally include a receiver to receive communications from a user device or the TV decoder device 102. In one example, the remote control device may be configured to wirelessly communicate with the performance evaluation apparatus 110.

Figure 3:
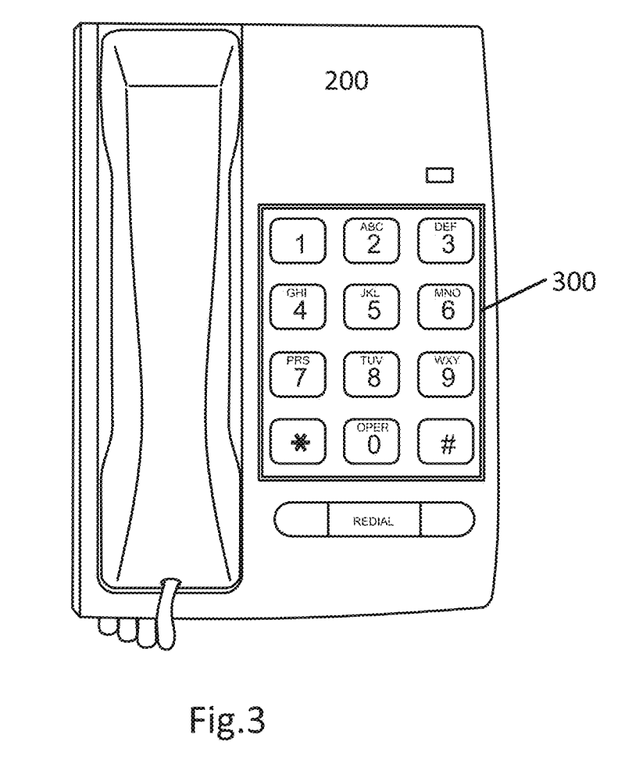
FIG. 3 illustrates a known landline phone and its button configuration.

The remote control device physical buttons are arranged in configuration that substantially matches the button configuration of a landline telephone. FIG. 3 illustrates an example of a landline telephone 200. The illustrative box 300 surrounds the buttons and the button configuration. The illustrative box 302 surrounds the buttons of the remote control device 104. As can be seen in FIG. 2 and FIG. 3, the button configuration of the remote control device 104 matches the button configuration of landline telephone.

The remote control 104 button configuration that matches the landline button configuration is advantageous because it is easy to use for elderly people. Most impaired users e.g., elderly users are also familiar with such a button configuration due to popularity of landline telephones that had been used for decades. The button configuration of the remote control device 104, as shown in FIG. 2 makes the remote control 104 intuitive to use for an impaired user.

Figure 4:
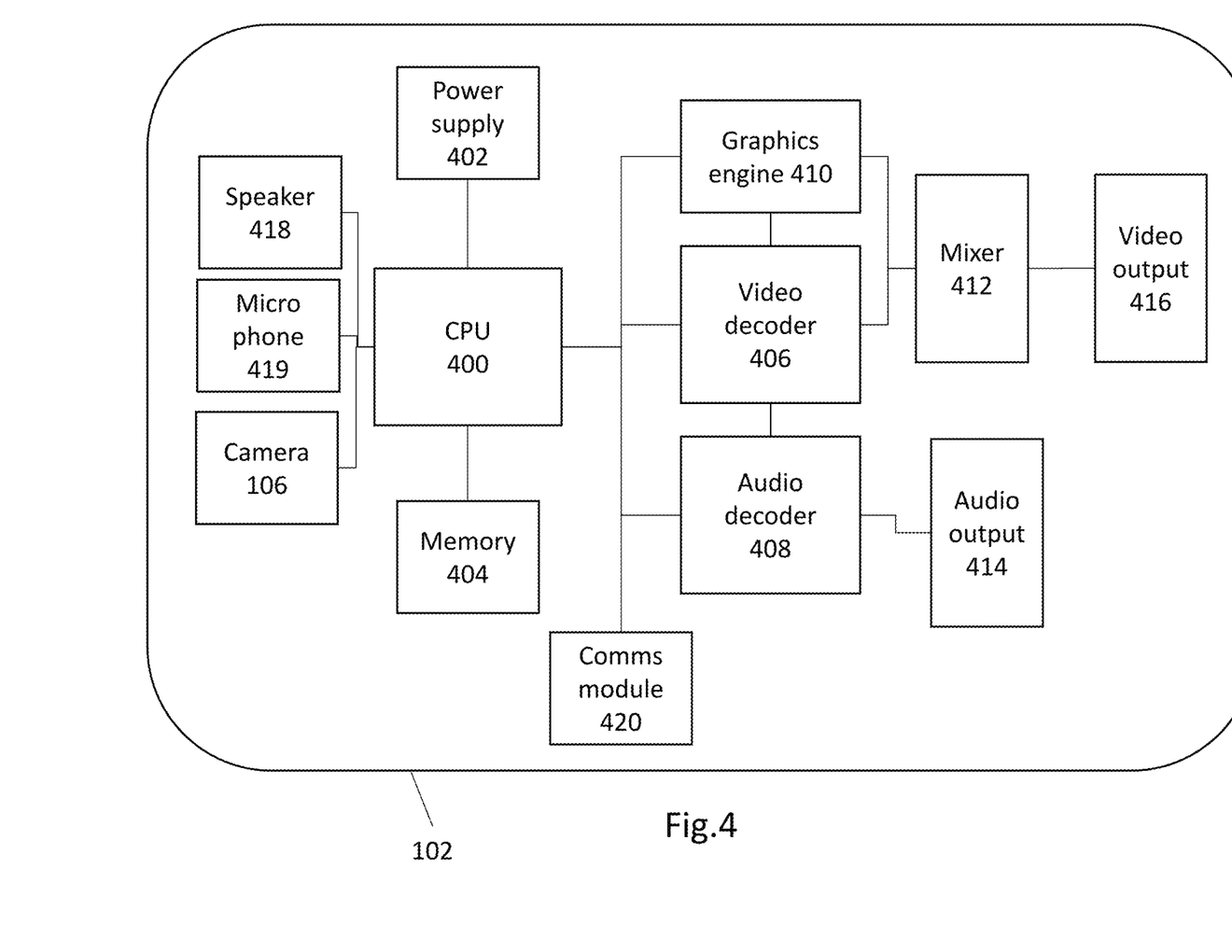
FIG. 4 illustrates a schematic of a TV decoder device of the system of FIG. 1.

FIG. 4 illustrates a schematic diagram of an example TV decoder device 102. The TV decoder device 102 (e.g., a TV set top box) comprises a main CPU 400, a power supply 402, a memory 404, a video decoder 406 and an audio decoder 408. The TV decoder device 102 may further comprise a graphics engine 410 and a mixer 412. The mixer 412 is electrically coupled to the graphics engine 410 and the video decoder 406. The audio decoder 408 may be coupled to an audio output 414, e.g., a digital or an analog output. The mixer 412 is coupled to a video output 416 that may be an analog or a digital output. The video output and audio output are coupled to the TV and provide video and audio content to the TV. The video content is presented on the TV and the audio content is outputted through the TV speakers.

The decoder device 102 comprises a camera 106, a speaker 418, a microphone 419 and a communications module 420. The communications module 420 may be a Wi-Fi module or a Bluetooth module or a cellular module. The comms module 420 allows the decoder device 102 to communicate using a suitable communications network. Optionally, the decoder device 102 may comprise a microphone that is configured to capture vocal inputs e.g., commands or sounds from a user.

Figure 5:
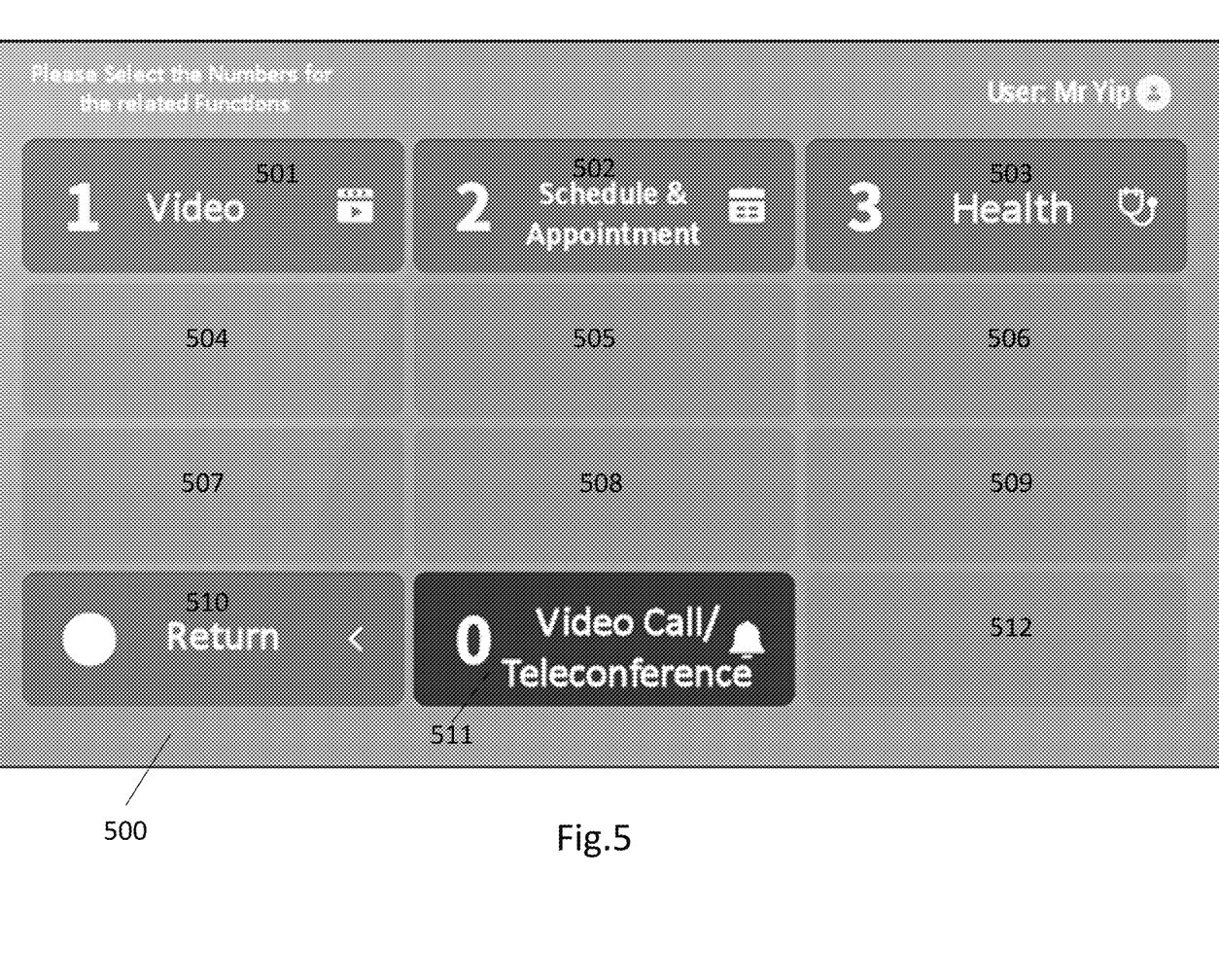
FIG. 5 illustrates an application interface of the TV decoder as presented on a TV screen with virtual buttons defining functions.
Figure 6:
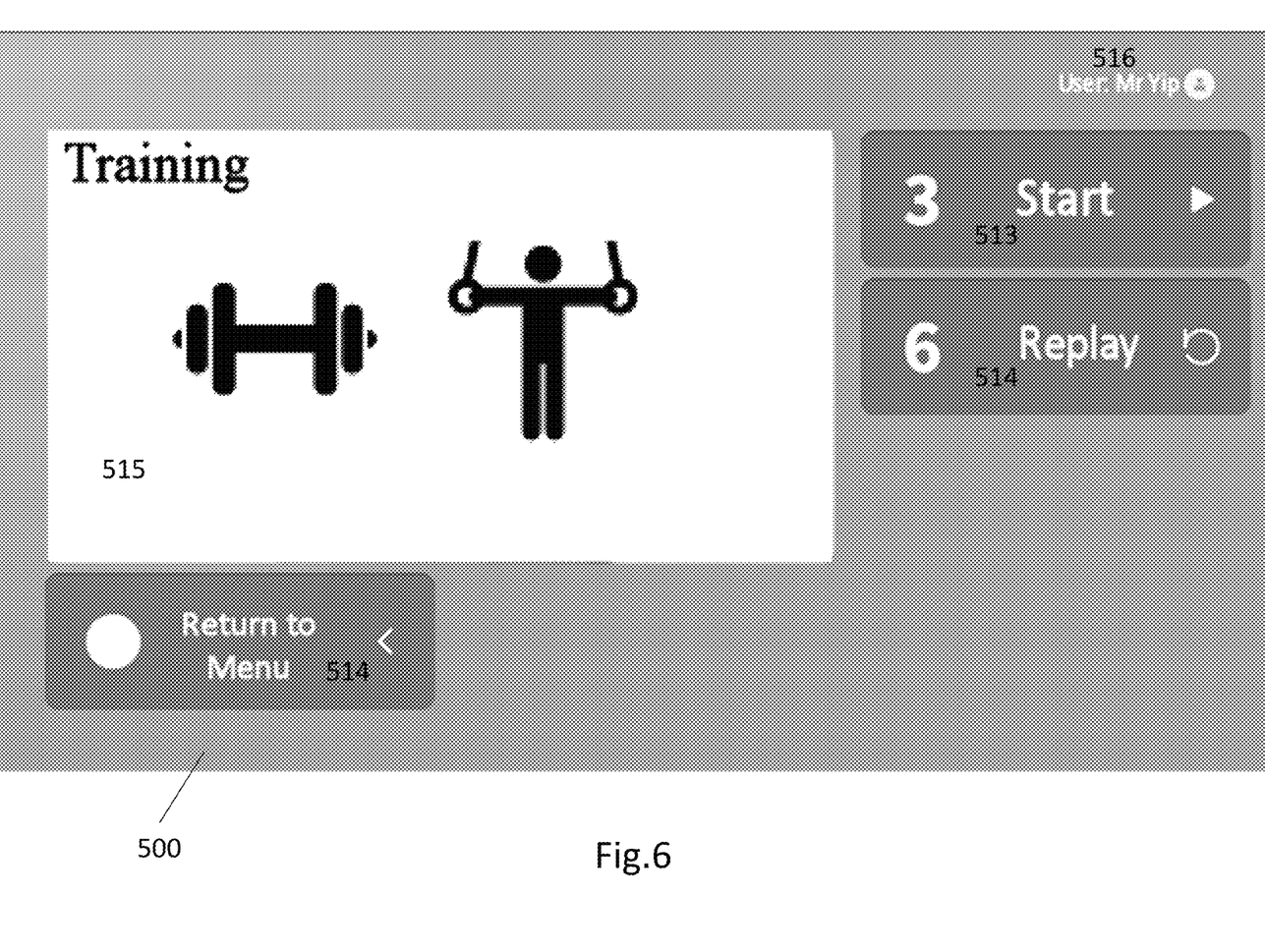
FIG. 6 illustrates an application interface with a training video and associated functions presented on the interface.

The TV decoder device 102 may comprise an application interface 500, as shown in FIG. 5 and FIG. 6. The application interface 500 is, in use, is presented on the TV 10. The application interface 500 defines one or more functions of the TV decoder device 102. The application interface 500 provides a screen that allows a user to interact with the decoder device 102 and control operations of the decoder device 102.

Referring to FIG. 5, The application interface 500 may comprise one or more buttons, wherein each button comprises an alphanumeric character or a symbol or a combination thereof. Each button may correspond to a function of the one or more functions. Meaning each button is associated with a single function. A button selected on the application interface 500 can cause a specific associated function to be performed by the decoder device 102. Each button being selectable from a user input at the remote control device 104.

The application interface buttons are activatable virtual buttons, wherein each virtual button is associated with a specific function of the TV decoder device 102. The application interface buttons are virtual buttons that correspond to the arrangement of the remote control device physical buttons.

In one example the application interface virtual buttons are arranged in a configuration that substantially matches a button configuration of a landline telephone. In one example the virtual buttons of the application interface 500 and physical buttons of the remote control 104 may be identical in configuration.

A physical button pushed on the remote control device 104 is configured to cause the corresponding application interface button to be activated. The TV decoder device 102 is configured to execute a function associated with the activated application interface button. Referring to FIG. 5, an example application interface and virtual buttons 501-512. The buttons may also include a numeral to match the remote control buttons. As shown in FIG. 5, button 501 has numeral 1 and the associated function is viewing a video e.g., a training video. Button 502 has numeral 2 and has the function of scheduling an appointment. Button 503 has numeral 3 and has the function of performing a health check. Button 511 has the numeral 0 and has the associated function of performing a video call or teleconference. Button 510 has the symbol < and function of return. Other virtual buttons may have unassigned functions that could be programmed into the decoder device 102. The programming of functions may be performed via the remote control device 104 or may be loaded into the memory or the decoder 102 may receive updated functions via the communication module 420.

Referring to FIG. 6, there is shown a further screen with additional virtual buttons. The buttons each comprise a numeral indicative of the corresponding physical button on the remote control. For example, as shown in FIG. 6, button 513 has the numeral 3 and corresponds to starting the video. Button 514 has the numeral 6 and corresponds to the function of replaying the video. These functions of the decoder 102 can be actioned by pressing the appropriate physical button having the corresponding numeral or symbol. For example, in FIG. 5 a user can press 0 on the remote control 104 to start a video call. In the example of FIG. 6, a person can press 3 button on the remote control device 104 to start the video.

A user may register for using the TV use assessment system 100. The user may be required to register with the performance evaluation apparatus 110 by following an appropriate registration process. Key user information such as name, age, physical or mental impairment etc may be captured and stored in the evaluation apparatus 110. A user may optionally login to the system 100 via the remote control, although a login may not be required in most domestic usage scenarios. The login may be captured by the decoder device 102, and a user name 516 is displayed on the application interface, as shown in FIG. 6. The login allows the decoder device to appropriately track the performance of a user.

The evaluation apparatus 110 may used by one or more therapists (e.g., physiotherapist, occupational therapist, physical therapist or appropriate practitioner) to monitor the user's interactions with the system 100 and evaluate the user's performance. The evaluation apparatus 110 may be configured to assess how well a user interacts with the remote control 104 and control the functions of the decoder device 102. This performance evaluation may comprise a performance score that is indicative of how well a user is interacting with the system. The performance score being generated by the performance evaluation apparatus 110. The performance score may be indicative of a user's risk of injury. The performance score may also be indicative of a user's physical health e.g., dexterity and hand-eye coordination. Additionally, the score may also be indicative of cognitive function e.g., can a user activate the appropriate functions or replicate the functions presented in a training video. The performance score may be indicative of both physical and mental health.

As part of determining a performance evaluation a training video is presented to the user on the TV 10. The decoder device 102 may include one or more predefined training videos that may be stored in the decoder device, e.g., in the memory. A particular training video may be presented on the TV. FIG. 6, illustrates an example application interface 500 with a training video 515 being presented on the interface 500. The video may include a specific number of actions a user has to perform. A user can control the video with appropriate functions e.g., virtual buttons 513, 514.

The TV decoder device 102 is configured to output a training video that is presented on the TV. The camera 106 is configured to record the interactions of the user with the system. The camera 106 is configured to record how well the user can follow the training video and use the remote control to select the functions indicated in the training video. The decoder device 102 may also record the buttons pressed by the user and how accurately and/or how quickly the buttons were pressed. The recorded video is stored in the decoder device 102 and transmitted to the performance evaluation apparatus 110. The performance evaluation apparatus 110 is configured to receive the recorded interactions from the decoder device 102. The evaluation apparatus 110 is further configured to compare the recorded interactions with the training video and generate the performance score based on the comparison of the recorded interactions and the training video. The evaluation apparatus 110 is configured to present the performance score on a display or transmitting the performance score to a therapist device.

Figure 7:
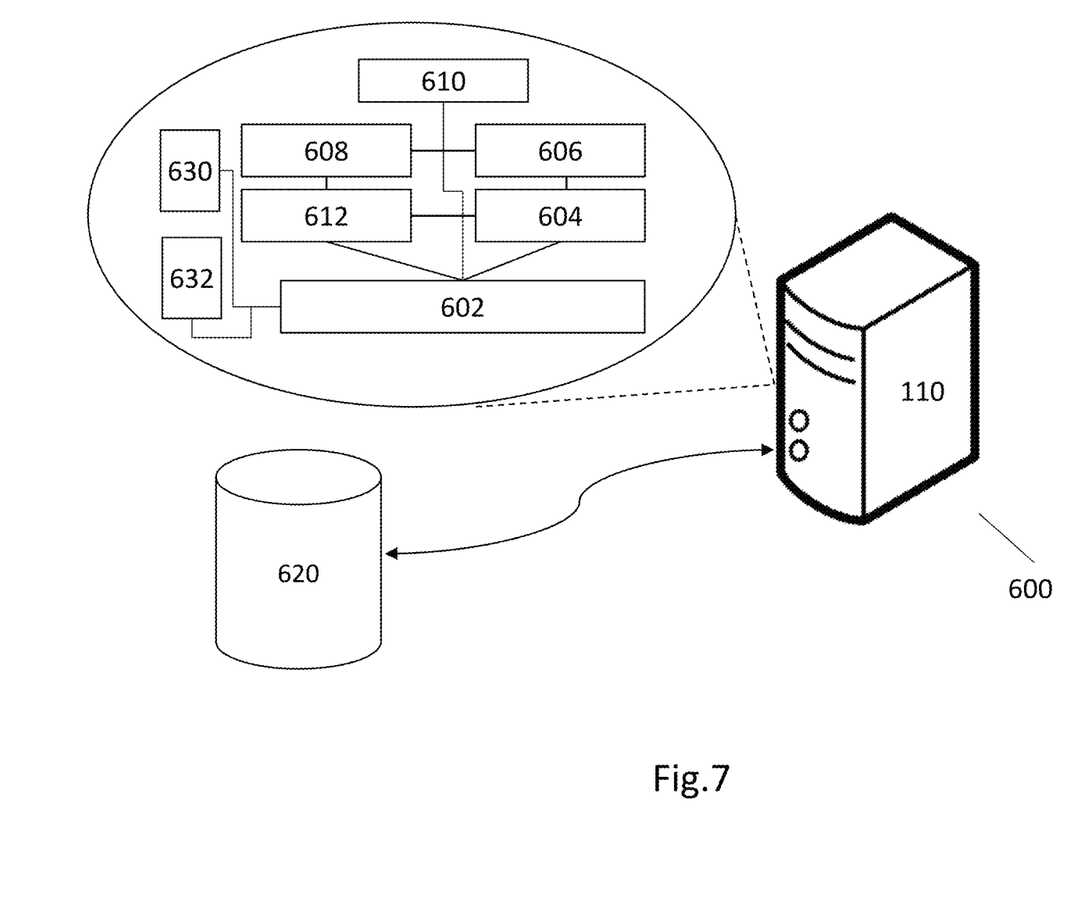
FIG. 7 illustrates a schematic diagram of an example performance evaluation apparatus.

In one example embodiment the performance evaluation apparatus 110 may be or may be implemented by a computing apparatus 600 having a processor, memory and other components. The performance evaluation apparatus 110 may be implemented by any computing architecture, including portable computers, tablet computers, stand-alone Personal Computers (PCs), smart devices, Internet of Things (IoT) devices, edge computing devices, client/server architecture, "dumb" terminal/mainframe architecture, cloud-computing based architecture, or any other appropriate architecture. The computing apparatus 600 may be appropriately programmed to implement the invention. The apparatus 600 may be appropriately programmed to receive the recording of the user interacting with the system and analyse the recording to generate an evaluation of the user interactions and perform other functions.

As shown in FIG. 7 there is a shown a schematic diagram of a computing apparatus or computer server 600 which is arranged to be implemented as an example performance evaluation apparatus 110. The evaluation apparatus 110 may be implemented as a server. In the illustrated embodiment of FIG. 7, the server 600 (i.e., evaluation apparatus 110) includes suitable components necessary to receive, store and execute appropriate computer instructions. The components may include a processor 602, including Central Processing Unit (CPU), Math Co-Processing Unit (Math Processor), Graphic Processing Unit (GPUs) or Tensor Processing Unit (TPUs) for tensor or multi-dimensional array calculations or manipulation operations, read-only memory (ROM) 604, random access memory (RAM) 606, and input/output devices such as disk drives 608, input devices 610 such as an Ethernet port, a USB port, etc. The decoder device 102 interacts with the TV display and may also comprise communications links 612 e.g. a comms module. The server 600, may comprise a user database 620 that is configured to store user information after a user registers with the system 100.

The server 600 (i.e., evaluation apparatus 110) may include instructions that may be included in memory and may be executed by the processor 602. There may be provided a plurality of communication links 612 which may variously connect to one or more computing devices such as a server, personal computers, terminals, wireless or hand-held computing devices, Internet of Things (IoT) devices, smart devices, edge computing devices. In one example, the communication links 612 allow communication with one or more decoder devices 102, and one or more therapist devices 108. At least one of a plurality of communications link may be connected to an external computing network through a telephone line or other type of communications link. The evaluation apparatus 110 may be structured to communicate with multiple decoders, each one associated with a specific user to assess the performance of multiple users. The evaluation apparatus 110 may be configured to communicate with multiple therapists via the therapist devices. The server 600 (i.e., evaluation apparatus 110) may also have a suitable operating system which resides on the disk drive or in the ROM of the server 100.

The computing apparatus 600 (or server) may also provide the necessary computational capabilities to operate or to interface with a machine learning network or an AI model, such as a neural network, to provide various functions and outputs. The neural network may be implemented locally, or it may also be accessible or partially accessible via a server or cloud-based service. The machine learning network may also be untrained, partially trained or fully trained, and/or may also be retrained, adapted or updated over time. The evaluation apparatus 110 may comprise the computational capabilities to implement one or more object recognition models. The object recognition models may be designed to detect objects e.g., a person or a person's hands and also detect and identify various actions being performed by the person.

The performance evaluation apparatus 110 is configured to receive the training video or may have the training video stored thereon e.g., in memory. In one example, a therapist may select a specific training video or upload a training video for a particular user. The training video may be downloaded by the decoder device 102 from the evaluation apparatus 110, via the communications module 420. Alternatively, the evaluation apparatus 110 may transmit a specified training video to the decoder 102 of a particular user. The evaluation apparatus 110 may be configured to compare the performance score with a performance threshold. The evaluation apparatus 110 is further configured to generate an alert if the performance score is less than the performance threshold. The evaluation apparatus 110 may be configured to transmit the alert and performance score to a therapist device and/or present the alert and performance score on the TV or on a display of the performance evaluation apparatus.

In one example a performance score less than a performance threshold is indicative of a user at risk of injury.

In one example the performance evaluation apparatus 110 may comprise a scoring module 630 and a risk module 632. The scoring module 630 may be configured to calculate the performance score based on the comparison between the recorded interactions and the training video. The risk module 632 may be configured to calculate a risk profile for a user based on the performance score calculated in the scoring module, the risk profile being indicative of the likelihood of an injury occurring to the user.

The scoring module 630 and risk module 632 may be software modules or parts of software code that may be executable by a processor of the performance evaluation apparatus. Alternatively, the scoring module and risk module may be hardware elements like microprocessors or programmable logic devices or FPGAs etc.

Figure 8:
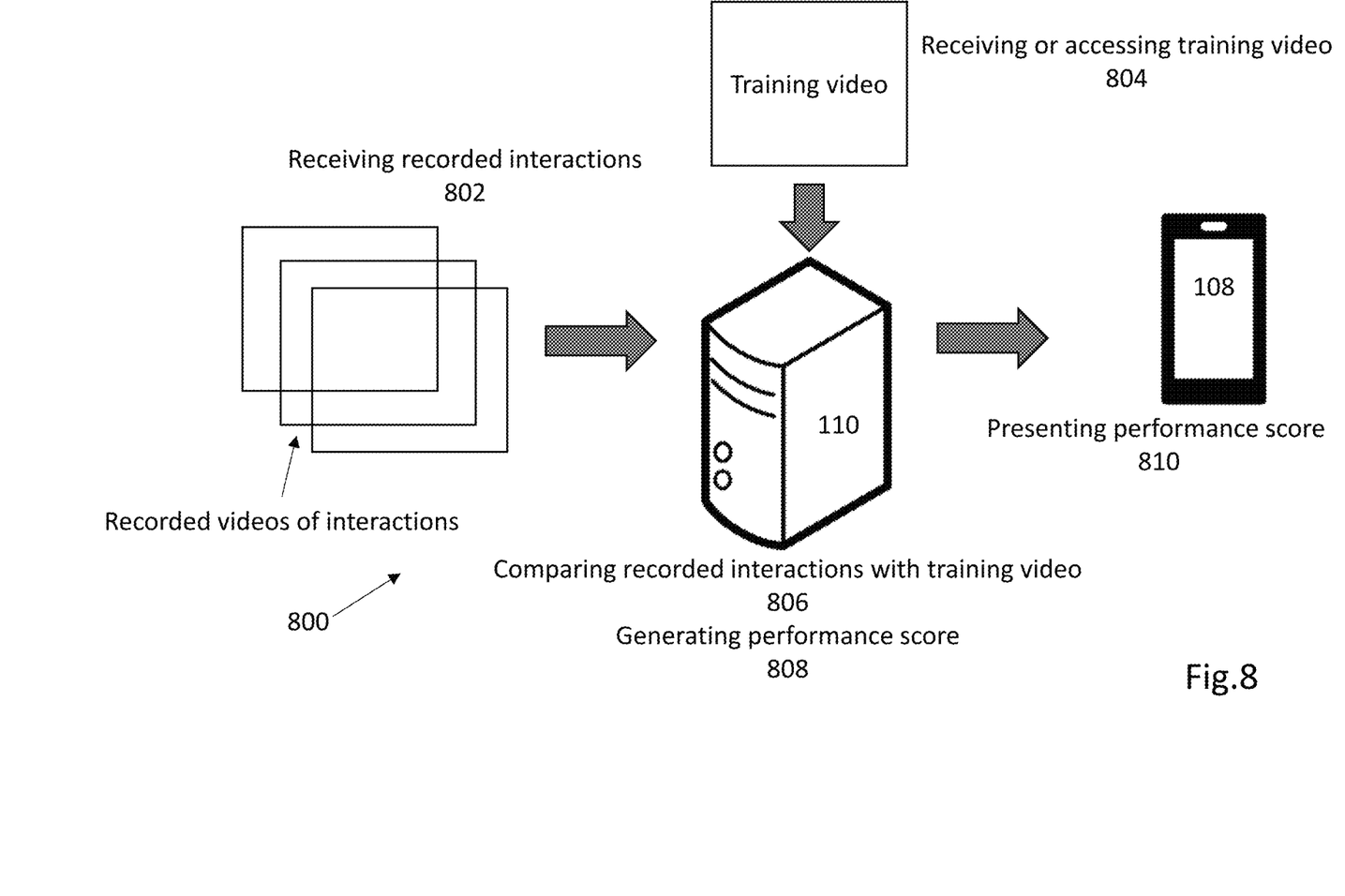
FIG. 8 illustrates a method of TV use assessment as implemented by the system of FIG. 1.

FIG. 8 illustrates a method of method of TV use assessment 800, as implemented by the system 100. Referring to FIG. 8, the method comprises step 802. Step 802 comprises receiving recorded interactions of a user with a remote control device 104 and a TV decoder device 102. The interactions may comprise recording the physical use of the remote control 104 and/or the selection of functions on the remote and application interface, as illustrated in the training video. The camera 106 may capture these interactions and the decoder device 102 may transmit recorded interactions to the evaluation apparatus 110.

Step 804 comprises receiving or accessing a training video that was presented to the user via the application interface 500. Step 806 comprises comparing the recorded interactions with the training video. At step 806, the performance evaluation apparatus 110 may be configured to perform an object recognition process on the recorded video and the training video to identify a user or one or more limbs of the user, identify the movements performed by the user and compare the identified movements with the training video. The comparison may be assessing how well a user performs the actions illustrated in the training video based on the buttons pressed on the remote. In one example, the performance evaluation may comprise a machine learning model or an AI model that is trained to execute an object detection process on the received recordings i.e., the received video recording and identify the interactions of the user with the remote control device and the TV decoder device.

The training video may be presented on the TV 10. Optionally, the speaker may be controlled to provide voice commands to a user to guide a user to use the TV remote device to control the application interface. The voice commands may be paired with the training video presented on the screen.

Step 808 comprises generating the performance score based on the comparison of the recorded interactions and the training video. As seen in FIG. 8, steps 806 and 808 are performed in the evaluation system 110. Step 808 may be executed by the scoring module 630.

Step 810 comprises presenting the performance score on a display or transmitting the performance score to a therapist device. In one example, the performance score is indicative of how well a user is interacting with the system. The performance score is an objective score calculated by the performance evaluation apparatus.

The risk module 632 may be configured to calculate a risk profile for a user based on the performance score calculated in the scoring module wherein the risk profile being indicative of the likelihood of an injury occurring to the user. In one example the risk module 632 is configured to calculate the risk profile based on the difference between performance score of the user and the performance threshold. The higher the performance score the lower the risk profile.

The method 800 may additionally comprise generating an alert if the performance score is less than the performance threshold at step 812. The alert may be transmitted to a therapist device. Additionally, the alert and performance score may be presented on the TV. A performance score less than a performance threshold is indicative of a user at risk of injury. The display of the score on the TV 10 allows a user to self-manage and assess their own progress or deterioration.

The TV use assessment system 100 is advantageous because the evaluation apparatus 110 generates an objective score of performance. The objective score is based on an automated assessment of how well a user performs functions presented in a training video. The system is advantageous as it provides an objective score and an objective performance assessment. This makes it easier for a therapist to track the user's current condition and improvement or deterioration of the user, rather than using subjective assessments (e.g., opinions) as is current practice. The TV use assessment system 100 further allows multiple users to be compared with each other since the system provides an objective score. The system provides a robust system that is easy to use for users and therapists. The system 100 is also advantageous as it is an automated system that can be used in a user's home. This means a user e.g. an elderly user does not need to go to a clinic or some other external facility. The assessment system 100 is advantageous for therapists since they receive performance scores and an evaluation on their phone or devices. Further the system 100 allows remove performance assessment of a user by a therapist thereby saving time and making the evaluation and assessment process simpler, quicker, cheaper and more efficient.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilised. This will include stand alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc., in a computer program. When a process corresponds to a function, its termination corresponds to a return of the function to the calling function or a main function.

The invention claimed is:

1. A television (TV) use assessment system comprising:
    a TV decoder device operatively coupled to a television (TV) and configured to receive signals, decode the received signals and provide an output to be presented on a TV,
    a remote control device configured to receive inputs from a user and transmit input signals to the TV decoder device,
    wherein the TV decoder device is configured to receive the input signals from the remote control device and perform one or more functions encoded within the input signals, and to output a training video that is presented on the TV,
    a camera configured to record user interactions with the system,
    a performance evaluation apparatus configured to:
        receive the recording of the user interacting with the system and analyse the recording to generate an evaluation of the user interactions, including receiving the recorded interactions, comparing the recorded interactions with the training video, generating the performance score based on the comparison of the recorded interactions and the training video, comparing the performance score with a performance threshold, generating an alert if the performance score is less than the performance threshold, transmitting the alert and performance score to a therapist device and/or present the alert and performance score on the TV or on a display of the performance evaluation apparatus, and presenting the performance score on a display or transmitting the performance score to a therapist device, wherein the performance evaluation is a performance score that is indicative of how well a user is interacting with the system, wherein a performance score less than a performance threshold is indicative of a user at risk of injury, and the performance score being generated by the performance evaluation apparatus.

2. The TV use assessment system of claim 1 wherein the performance evaluation apparatus comprises:
a scoring module configured to calculate the performance score based on the comparison between the recorded interactions and the training video, and
a risk module configured to calculate a risk profile for a user based on the performance score calculated in the scoring module, the risk profile being indicative of the likelihood of an injury occurring to the user.

3. The TV use assessment system of claim 2 wherein the risk module is configured to calculate the risk profile based on the difference between performance score of the user and the performance threshold, wherein the higher the performance score the lower the risk profile.

4. The TV use assessment system of claim 1 wherein the camera is configured to detect a video of a user interacting with the remote control device and providing inputs to the TV decoder.

5. The TV use assessment system of claim 4 wherein the recorded interactions are a video of the user's interactions with the system, and the performance evaluation apparatus configured to perform an object recognition process on the recorded video and the training video to: identify a user or one or more limbs of the user, identify the movements performed by the user and compare the identified movements with the training video.

6. The TV use assessment system of claim 5 wherein the performance score is an objective score calculated by the performance evaluation apparatus.

7. The TV use assessment system of claim 6 wherein the TV decoder device comprises:
an application interface that, in use, is presented on the TV,
wherein the application interface defines one or more functions of the TV decoder device,
the application interface comprises one or more buttons, wherein each button comprises an alphanumeric character or a symbol,
each button corresponding to a function of the one or more functions, and;
each button being selectable from a user input at the remote control device.

8. The TV use assessment system of claim 7 wherein the application interface comprises at least twelve buttons, at least two buttons comprising a symbol and at least ten buttons comprising numerals.

9. The TV use assessment system of claim 8 wherein the remote control device comprises a plurality of physical buttons,
the application interface buttons are activatable virtual buttons, wherein each virtual button is associated with a specific function of the TV decoder device,
wherein the application interface buttons are virtual buttons that correspond to the arrangement of the remote control device physical buttons, such that a physical button pushed on the remote control device is configured to cause the corresponding application interface button to be activated, and;
the TV decoder device is configured to execute a function associated with the activated application interface button.

10. The TV use assessment system of claim 9 wherein the application interface virtual buttons are arranged in a configuration that substantially matches a button configuration of a landline telephone, and the remote control device physical buttons are arranged in configuration that substantially matches the button configuration of a landline telephone, and wherein the virtual buttons and physical buttons are identical in configuration.

11. The TV use assessment system of claim 10 wherein TV decoder is a TV set top box and the camera is integrated into the TV decoder.

12. The TV use assessment system of claim 11 comprises a speaker, the speaker being operatively coupled to the TV decoder device and controlled to provide voice commands to a user to guide a user to use the TV remote device to control the application interface.

* * * * *